CHRYSANTHEMUM PLANT

Filed Sept. 23, 1970 2 Sheets-Sheet 1

INVENTORS
WALTER H. JESSEL, JR.,
WILLIAM E. DUFFETT
BY
Oberlin, Maky, Donnelly & Renner
ATTORNEYS

United States Patent Office

Plant Pat. 3,189
Patented May 23, 1972

3,189
CHRYSANTHEMUM PLANT

Walter H. Jessel, Jr., Doylestown, and William E. Duffett, Akron, Ohio, assignors to Yoder Brothers, Inc., Barberton, Ohio

Filed Sept. 23, 1970, Ser. No. 74,941
Int. Cl. A01h *5/00*
U.S. Cl. Plt.—74 1 Claim

The present invention comprises a new and distinct variety of chrysanthemum plant which is a seedling of #6593–1 × #6513–2. Both of these parents are unpatented and are identified by such numbers for breeding purposes to distinguish the same from other parents in the same breeding program.

The new variety is similar in many respects to Tuneful, an unpatented but well-known commercial variety of Yoder Brothers, Inc., Barberton, Ohio, assignee of the present invention. The new variety has the same characteristics as Tuneful of:

(1) Daisy form.

(2) Productive compound spray.

The new variety is distinguished from Tuneful by the following characteristics:

(1) A lighter pastel color ranging from golden bronze in low light to honey yellow in high light, high temperature periods.

(2) More rounded petals.

(3) A faster, more uniform response under marginal 60° night temperatures as well as the high temperature periods of summer. Tuneful does not tolerate these extremes as well.

(4) Plants establish themselves 4–7 days earlier for pinching.

(5) Superior breaking action as a pot plant or pinched cut flower.

(6) Better pot mum habit.

(7) Flowers provide superior lasting qualities. Discs mature at a slower rate and shed less pollen. Dramatic has superior keeping qualities and color retention under home conditions, keeping and holding color 14–20 days compared to 7–10 for Tuneful.

The new variety was selected from the progeny of the designated cross and when asexually reproduced by cuttings at Barberton, Ohio, has been found to retain its distinctive characteristics through successive propagations.

Our new variety when grown in the vicinity of Barberton, Ohio, has a response period of approximately 9 weeks. The response time, color and blooming period may vary significantly with varying environmental conditions such as temperature, day length, and light intensity.

The following chart outlines the variation in response experienced in Barberton, Ohio, with carbon dioxide injected into the greenhouse atmosphere when applicable when the plant is grown for different uses:

| Season | Daisy pompon | Disbudded pot mum | Spray pot mum |
|---|---|---|---|
| Spring | Early 9 week | Mid 8 week | Early 9 week. |
| All other seasons | Mid 9 week | Early 9 week | Mid 9 week. |

Suggested flowering in the northern, western, and southern United States is year round as a pot mum. In the northern and western United States, April through November as a daisy pompon, and in the South year round as a daisy pompon.

Figure 1:
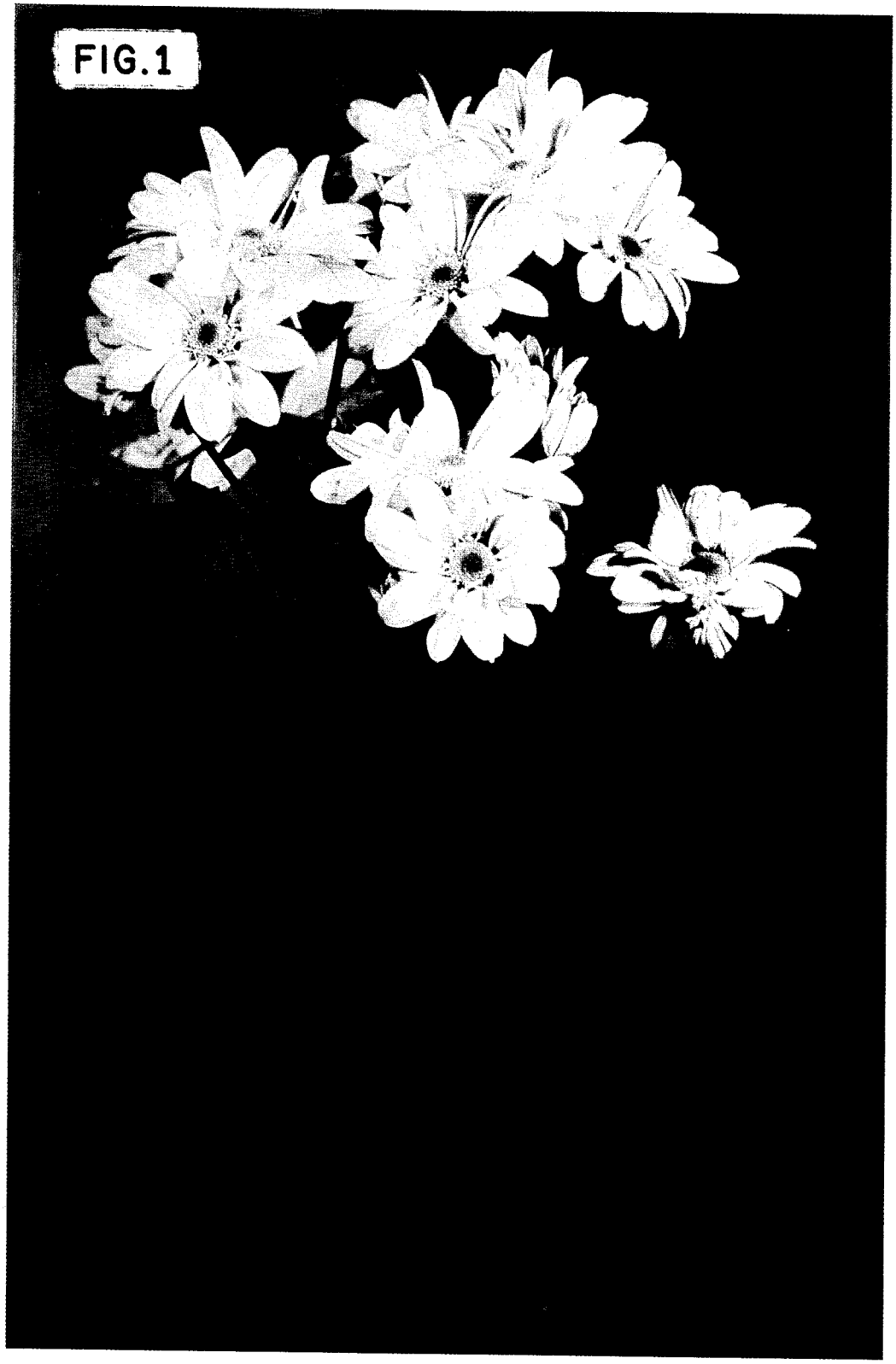
Figure 2:
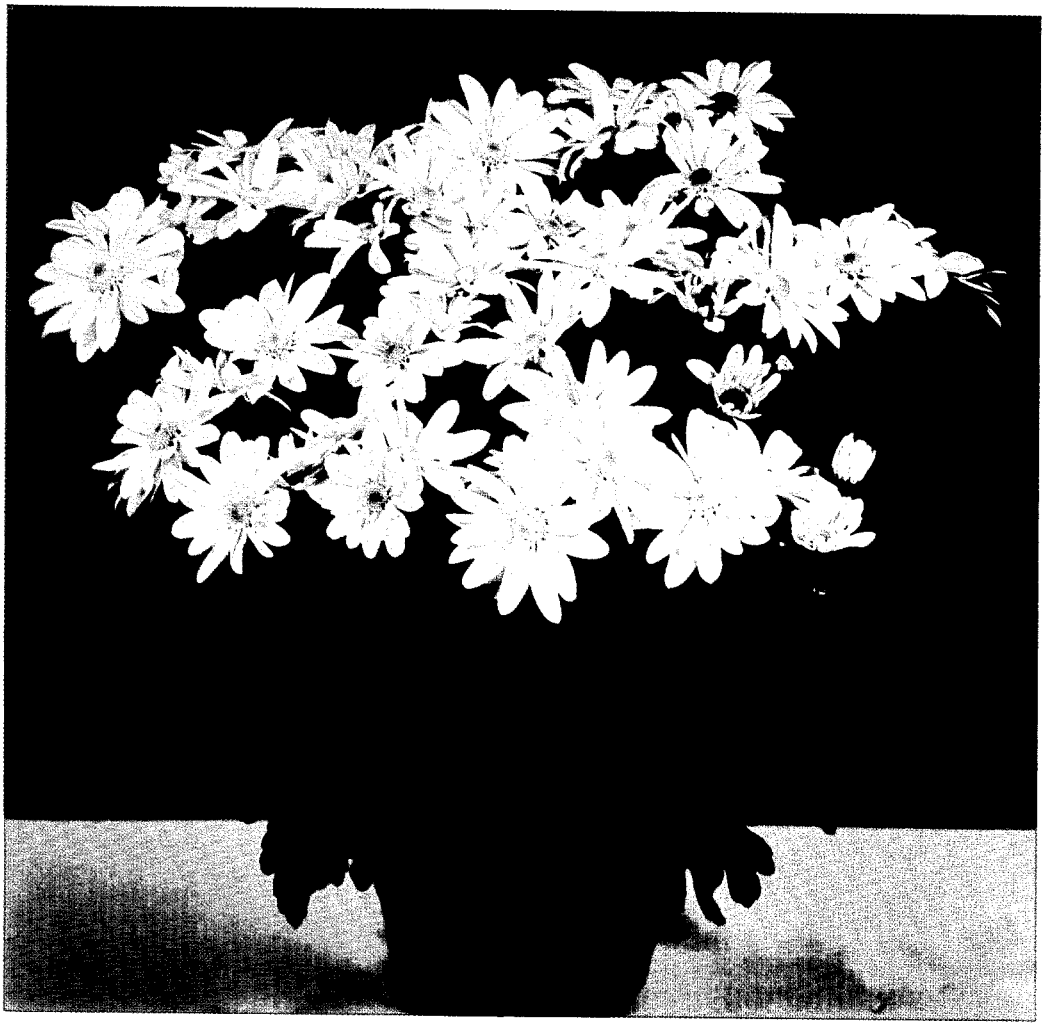

The accompanying drawings show the unique characteristics of our new variety, the colors being as nearly true as possible with color illustrations of this type. FIG. 1 shows the new variety as a daisy pompon and FIG. 2 shows the new variety as a daisy pot mum.

The following data is based on observations made of the new variety in a greenhouse in Barberton, Ohio. Color references are to the Munsell Color Book, 1963 edition, and comparisons are made with the cultivar Tuneful.

Botanical classification: *Chrysanthemum morrifolium*

| | Dramatic | Tuneful |
|---|---|---|
| Bloom: | | |
| Size | 2½″–3½″ | 2¼″–3¼″. |
| Fully expanded | 4″ | 3¼″. |
| Borne | Cluster on elongated pedicel. | Cluster on elongated pedicel. |
| Stems | Elongated pedicels 8″–12″ long. | Elongated pedicels 6″–10″ long. |
| Form | Daisy (single) | Daisy (single). |
| Permanence | 14 to 20 days | 7 to 10 days. |
| Color (Munsell)— | | |
| Center of flower | Yellow green, 5GY5/6 to 5Y8/14. | Yellow green, 5GY5/6 to 5Y8/14. |
| Base of petals | Yellow bronze, 8.75YR7/12 to yellow, 5Y8/10. | Yellow bronze, 2.5Y7/10 to bronze, 10R4/8. |
| Inside of petals | do | Red bronze to 10R4/10, yellow bronze, 2.5Y7/10. |
| Reverse of petals | Yellow, 5Y8/10 to light yellow, 5Y8.5/10. | Light bronze, 10YR7/6. |
| Tonality from a distance. | Golden bronze to yellow depending on finishing temperatures. | Orange bronze. |
| Discoloration | Golden tonal yellow from distance. | Light bronze. |

Petals: (The following data also applies to Tuneful).

*Texture.*—Smooth.

*Appearance and form.*—Keeled, tapering to a rounded point.

*Arrangement.*—Composite, whorled on a single receptacle.

*Persistence.*—Resists shatter.

*Fragrance.*—Typical chrysanthemum.

Reproductive organs:

*Stamen, anthers.*—200 or more.

*Pollen.*—Abundant to none (functional sterility).

*Arrangement.*—Clustered in center of flower.

*Styles.*—Present in both ray and disc florets.

*Length.*—Short.

*Ovaries.*—At base of petals attached to receptacle.

| | Dramatic | Tuneful |
|---|---|---|
| Plant: | | |
| Form | Herbaceous | Herbaceous. |
| Growth | Semi-upright | Semi-upright. |
| Height | 32″–36″ as a cut pompon. | 28″–32″ as a cut pompon. |
| Spread | 12″–20″ as a pot mum | 12″–18″ as a pot mum. |
| Foliage: | | |
| Top side | Dark green, 10GY3/4 | Dark green, 10GY2/4. |
| Size | 5½″ long, 3″ wide | 3¼″ long, 2¼″ wide. |
| Quantity | Numerous | Numerous. |
| Shape | Spatulate lobed | Spatualte lobed. |
| Texture | Smooth | Smooth. |
| Ribs and veins | Prominent | Prominent. |
| Edge | Indented | Deeply indented. |
| Serration | Sharply serrated | Moderately serrated. |
| Underside | Light green, 7.5GY4/4 | Light green, 7.5GY4/4. |
| Stipules | Base of petiole | Base of petiole. |

We claim:

1. A new and distinct variety of chrysanthemum characterized particularly by its unique pastel color which ranges from gloden bronze in cooler, darker weather to honey yellow in high light, high temperature periods; its superb and improved lasting qualities both as a cut flower and a pot plant; its excellent pot habit, unique in presently existing daisy types; its more uniform and faster response under low and high temperature conditions, compared to the cultivar Tuneful; and its tendency for plants to establish themselves 4–7 days earlier than Tuneful for pinching.

No references cited.

ROBERT E. BAGWILL, Primary Examiner

UNITED STATES PATENT OFFICE
CERTIFICATE OF CORRECTION

Patent No. PP 3,189 Dated May 23, 1972

Inventor(s) WALTER H. JESSEL, JR. and WILLIAM E. DUFFETT

It is certified that error appears in the above-identified patent and that said Letters Patent are hereby corrected as shown below:

In column 2, line 19, "morrifolium" should be --morifolium--.

In column 2, approximately line 34, adjacent the heading "Inside of Petals" and under the cultivar heading "Tuneful", change "to 10R4/10" to --, 10R4/10 to--.

In claim 1, line 3, "gloden" should be --golden--.

Signed and sealed this 2nd day of October 1973.

(SEAL)
Attest:

EDWARD M.FLETCHER,JR.
Attesting Officer

RENE D. TEGTMEYER
Acting Commissioner of Patents